United States Patent [19]

Thornton

[11] Patent Number: 5,573,508
[45] Date of Patent: Nov. 12, 1996

[54] CATHETER WITH AN EXPANDABLE PERFUSION LUMEN

[75] Inventor: Troy L. Thornton, San Francisco, Calif.

[73] Assignee: Advanced Cardiovascular Systems, Inc., Santa Clara, Calif.

[21] Appl. No.: 343,182

[22] Filed: Nov. 22, 1994

[51] Int. Cl.$^6$ .................................................. A61M 25/00
[52] U.S. Cl. .............................................. 604/96; 606/194
[58] Field of Search ........................... 604/96, 98, 99, 604/101, 102, 282, 281, 107; 606/194

[56] References Cited

U.S. PATENT DOCUMENTS

| | | | |
|---|---|---|---|
| 5,344,402 | 9/1994 | Crocker | 604/96 |
| 5,364,357 | 11/1994 | Aase | 604/282 X |
| 5,383,890 | 1/1995 | Miraki et al. | 604/96 X |
| 5,409,460 | 4/1995 | Krumme | 604/107 |
| 5,409,470 | 4/1995 | McIntyre et al. | 604/282 X |

*Primary Examiner*—John D. Yasko
*Attorney, Agent, or Firm*—Heller, Ehrman, White & McAuliffe

[57] ABSTRACT

An intravascular catheter such as a dilatation catheter for angioplasty procedures which is provided with a perfusion lumen extending which is expanded when disposed within a desired location with the patient's body lumen so as to increase the perfusion of body fluid such as oxygenated blood through the perfusion lumen.

20 Claims, 5 Drawing Sheets

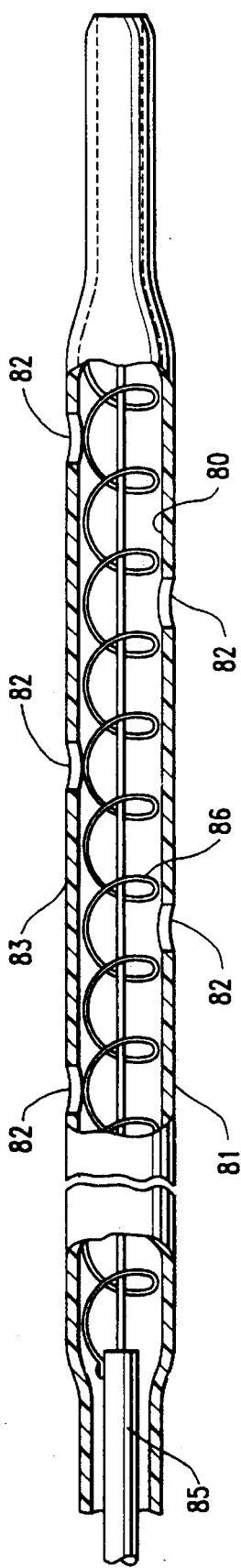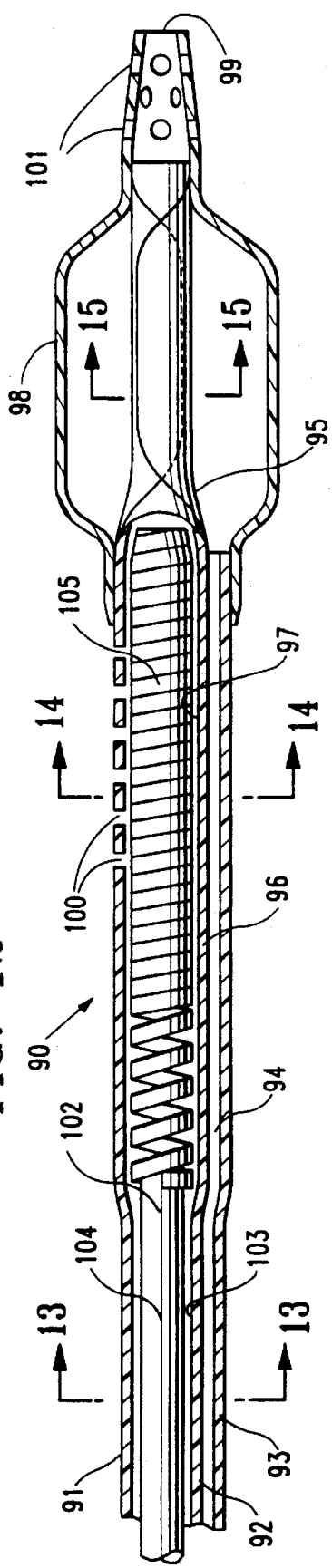

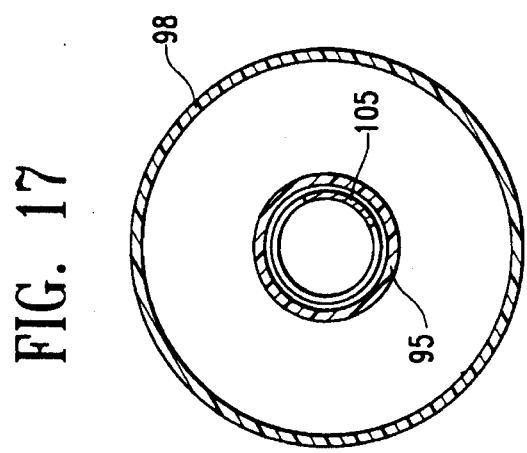
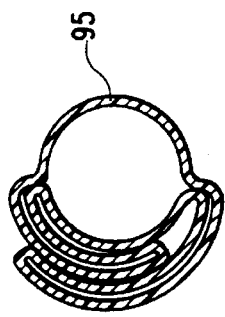
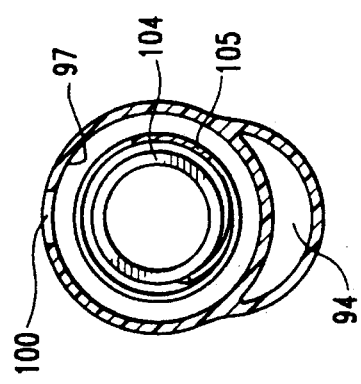
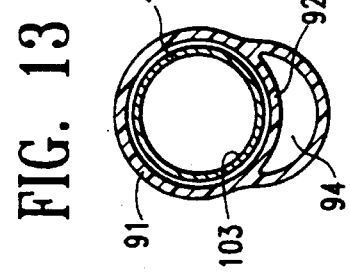
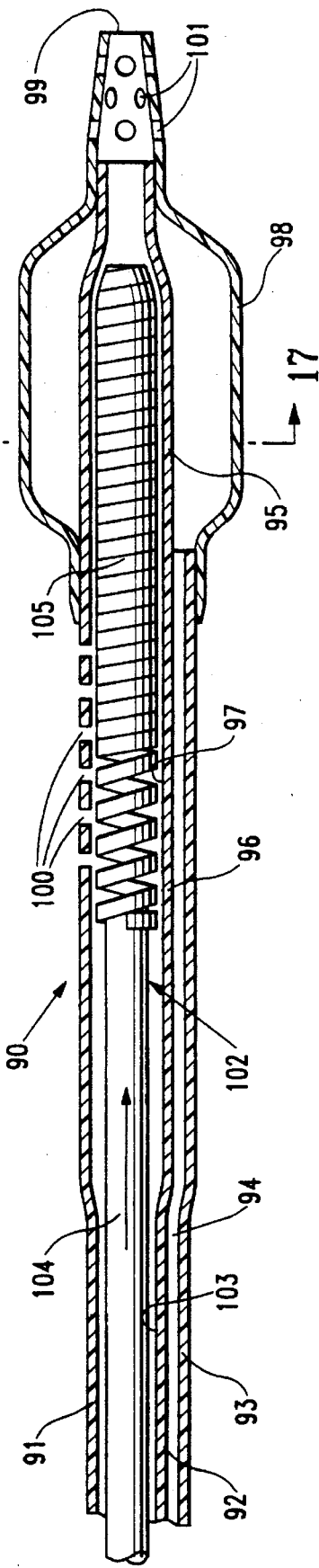

CATHETER WITH AN EXPANDABLE PERFUSION LUMEN

BACKGROUND OF THE INVENTION

This invention generally relates to the field of intravascular catheters, and more particularly to a dilatation catheter for percutaneous transluminal coronary angioplasty (PTCA) having perfusion capabilities.

PTCA is now one of the most widely used treatment modalities for heart disease. The procedure basically comprises advancing a dilatation catheter, having an inflatable balloon on the distal portion thereof, into the patient's coronary anatomy until the balloon of the dilatation catheter is properly positioned across the lesion to be dilated. Once properly positioned, the dilatation balloon is inflated with liquid to a predetermined size at relatively high pressures to expand the arterial passageway. Generally, the inflated diameter of the balloon is approximately the same diameter as the native diameter of the body lumen being dilated so as to complete the dilatation but not overexpand the artery wall. After the balloon is finally deflated, blood flow resumes through the dilated artery and the dilatation catheter can be removed therefrom.

Long term dilatation has many clinical advantages, including the elimination of sudden occlusion of an arterial passageway due to an arterial dissection. However, in order to effect long term dilatation, some provision must be made to perfuse oxygenated blood distal to the catheter during the long term dilatation. One perfusion-type dilatation catheter which has met with a great deal of commercial success is the RX® Perfusion Dilatation Catheter which is available from the assignee of the present invention, Advanced Cardiovascular Systems, Inc. The latter catheter has recently been replaced by a perfusion dilatation catheter sold by the present assignee under the trademark FlowTrack which has met with even more commercial success. These perfusion catheters have a plurality of perfusion ports in the wall forming at least part of the catheter body proximal to the balloon which are in fluid communication with a guidewire receiving perfusion lumen extending to the distal end of the catheter body. A plurality of perfusion ports are also preferably provided in the catheter body distal to the balloon which are also in fluid communication with the inner lumen extending to the distal end of the catheter body. When the balloon on the distal extremity of the dilatation catheter is inflated to dilate a stenosis, oxygenated blood in the artery or the aorta or both, depending upon the location of the dilatation catheter within the coronary anatomy, is forced to pass through the proximal perfusion ports, through the inner lumen of the catheter body and out the distal perfusion ports. This provides oxygenated blood downstream from the balloon while it is inflated to thereby prevent or minimize ischemic conditions in tissue distal to the catheter. The balloon can be inflated for long term dilatations with no tissue damage due to ischemia distal to the catheter. As is appreciated by those skilled in the art, tissue distal to a stenosis is frequently already in jeopardy due to ischemic conditions which may exist due to the stenotic blockage. As a result, care is exercised in sizing the perfusion ports and the inner lumen to ensure that there is adequate flow of oxygenated blood to tissue distal to the catheter. Unfortunately, commercially available perfusion catheters continue to have relatively large profiles due to the relatively large lumens required to perfusion sufficient quantities of oxygenated blood. The large profile of these catheters can prevent their use in distal coronary locations.

What has been needed is a perfusion type dilatation catheter which has a lower profile than those presently available but which can perfusion adequate quantities of oxygenated blood distal to the catheter to prevent ischemia when the balloon thereon is inflated.

SUMMARY OF THE INVENTION

The present invention is directed to an intravascular catheter, such as a dilatation catheter for angioplasty procedures, which has a low profile while it is being advanced through the patient's body lumen but which has a perfusion lumen which can be expanded to increase the flow of body fluid, such as oxygenated blood, therethrough when an occlusion means on a distal portion of the catheter occludes the body lumen or when the body lumen is occluded by other means such as a sudden collapse of a dissected arterial lining or an arterial spasm.

The intravascular catheter of the invention generally has an elongated catheter shaft with proximal and distal ends, a port or opening in the distal end and a perfusion lumen extending within at least a distal portion of the catheter shaft from one or more perfusion opening or ports proximal to the distal end to the port in the distal end. Means are provided to expand the perfusion lumen particularly the portion extending with the balloon on the distal end of the catheter shaft, so that when the catheter is disposed within a body lumen which is occluded naturally or by means such as the balloon provided on the catheter body, fluid can more readily pass through the perfusion lumen.

A presently preferred embodiment of the invention is a perfusion type dilatation catheter which has an elongated catheter shaft with proximal and distal ends, an inflation lumen extending within the catheter shaft to a location on a distal section of the shaft spaced proximal to the distal end, a dilatation balloon on the distal section having an interior in fluid communication with the inflation lumen, a guidewire receiving perfusion lumen extending at least within the distal section from a location proximal to the balloon to the distal end of the catheter shaft, at least one perfusion port in the catheter shaft proximal to the balloon in fluid communication with the guidewire receiving perfusion lumen and a guidewire port in the distal end of the catheter shaft in fluid communication with the guidewire receiving perfusion lumen. The system is applicable for over-the-wire and rapid exchange type catheters. The tubular member defining the perfusion lumen may be formed out of elastic material which will provide an elastic expansion or an inelastic material longitudinally folded about itself which allows expansion by unfolding.

In accordance with the present invention, means are provided within at least a portion of the guidewire receiving perfusion lumen to expand the interior of the perfusion lumen to increase the flow of oxygenated blood through the lumen when the inflated dilatation balloon occludes the arterial passageway. A variety of suitable means to expand the perfusion lumen are contemplated and will be readily apparent to those skilled in the art.

For example, one means devised is an elongated highly torquable tubular member with a helical coil secured by its proximal end to the distal end of the tubular member and extending distal to the tubular member and an operating shaft extending through the tubular member and the coil and being secured by its distal end to the distal end of the coil.

The expandable means is advanced through the perfusion lumen until the coil is at a desired location therein and then relative rotation is effected between the operating shaft and the tubular member to expand the helical coil which in turn expands the perfusion lumen of the catheter. Upon completion of the dilatation and deflation of the balloon, relative rotation may then effected between the tubular member and the operating shaft in a direction opposite to the first rotation to contract the helical coil and facilitate its removal.

Another system for providing an expanded perfusion lumen involves forming the portion of the tubular member which will define the portion of the perfusion lumen to be expanded from inelastic polymer materials such as polyetheylene and expanding the expandable portion to the desired expanded size and then folding the expanded portion about itself to form smaller transverse cross-sectional dimensions, preferably smaller than the transverse cross-sectional dimensions of the inner tubular member adjacent to the expandable section. A coil or other expanding member is slidably disposed within the tubular member adjacent to the expandable perfusion lumen and is advanced into the expandable perfusion lumen. The coil inserted may be expandable as described above or it may have an outer diameter sufficient to expand the perfusion lumen. A cylindrically shaped tube may also be similarly used.

Another means, similar to the first means, has a highly torqueable tubular member with an expandable cage of braided, high strength strands such as wires which is secured to the distal end of the tubular member. A control line extends through an inner lumen of the tubular member and the interior of the expandable cage and is secured to the distal end of the expandable cage. Movement of the ends of the cage toward one another increases the cage's diameter which in turn is utilized to expand the perfusion lumen to increase blood flow therethrough when the balloon is inflated. Upon deflation of the balloon, the ends of the cage may then be moved apart to reduce the diameter of the cage to facilitate the removal of the expandable means.

Another means for expansion of the perfusion lumen includes an expandable member similar to a stent, such as an elongated helical coil, disposed within the perfusion lumen or incorporated within the cylindrical wall of the inner tubular member and formed of a shape memory alloy adapted to expand upon reaching either body temperature or a temperature above body temperature which does not damage tissue within the arterial passageway. Another means includes a self expandable member such as a cage which is covered with a sheath to prevent expansion while being advanced within the body lumen but which expands when the sheath is removed.

The expandable perfusion lumen of the invention allows the use of a much lower profile catheter shaft than existing perfusion catheters yet still provides for adequate perfusion of body fluid to a location distal to the catheter. These and other advantages of the invention will become more apparent from the following detailed description thereof when taken in conjunction with the accompanying exemplary drawings.

BRIEF DESCRIPTION OF THE DRAWINGS

FIG. 11 is a longitudinal cross-sectional view of a bail-out type intravascular catheter embodying features of the invention.

FIG. 12 is an elevational view, partially in section, of an alternative perfusion dilatation catheter embodying features of the invention.

FIG. 13 is a transverse cross-sectional view of the catheter shown in FIG. 12 taken along the lines 13—13.

FIG. 14 is a transverse cross-sectional view of the catheter shown in FIG. 12 taken along the lines 14—14.

FIG. 15 is a transverse cross-sectional view of the catheter shown in FIG. 12 taken along the lines 15—15.

FIG. 16 is an elevational view partially is section of the alternative embodiment shown in FIG. 12 with an expanded perfusion lumen.

FIG. 17 is a transverse cross-sectional view of the catheter shown in FIG. 16 taken along the lines 17—17.

DETAILED DESCRIPTION OF THE INVENTION

Figure 1:
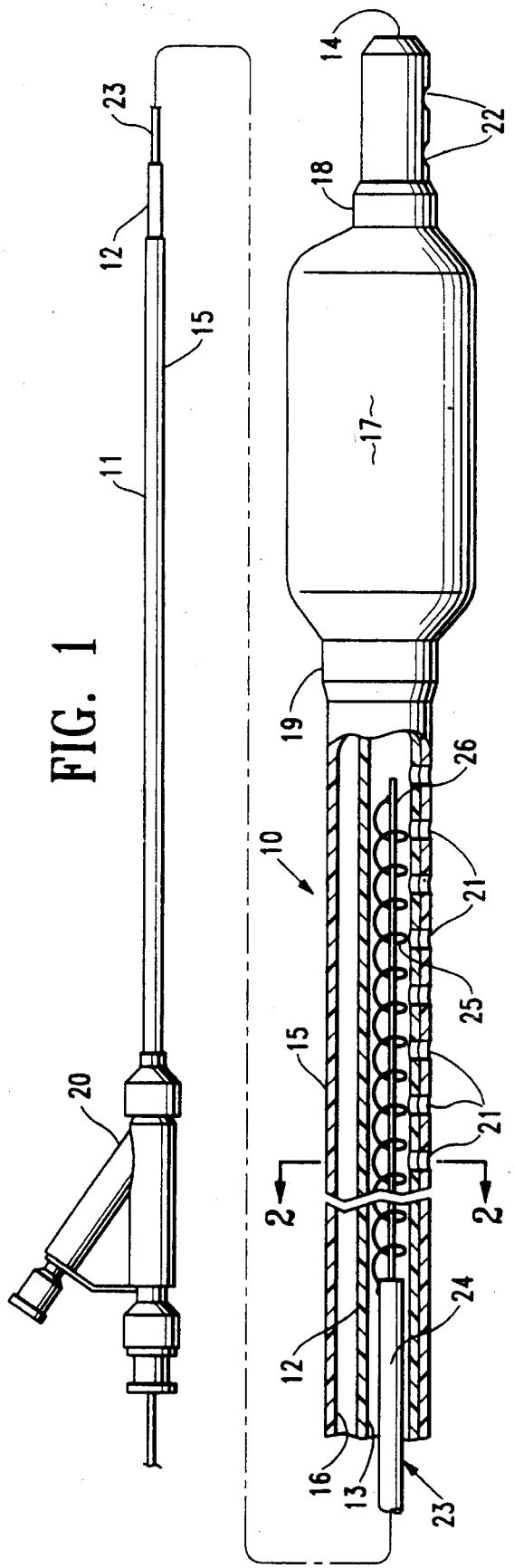
FIG. 1 is an elevational view, partially in section, of a perfusion dilatation catheter embodying features of the invention.

FIGS. 1–4 schematically illustrate an over-the-wire, perfusion-type dilatation catheter 10 embodying features of the invention. The catheter 10 generally includes an elongated catheter shaft 11 which has an inner tubular member 12 with a guidewire receiving perfusion lumen 13 extending to a guidewire port 14 in the distal end of the catheter shaft, an outer tubular member 15 disposed about the inner tubular member and defining therebetween an inflation lumen 16 extending through the catheter body to a location spaced proximally from the distal end of the catheter shaft. A inflatable dilatation balloon 17 is mounted on a distal portion of the catheter shaft 11 with the distal end or skirt 18 of the balloon being secured in a suitable manner to the distal extremity of the inner tubular member 12 which extends through the interior of the balloon and with the proximal end or skirt 19 of the balloon being secured in a suitable manner to the distal end of the outer tubular member 15. The dilatation balloon 17 may also be formed from the same tubing as the outer tubular member 15 in a unitary construction as is well known to those skilled in the art. A multiarm adapter 20 is secured to the proximal ends of the inner and outer tubular members 13 and 15, respectively.

The inner tubular member 12 is secured in a suitable manner to the interior of the outer tubular member 15 along a length thereof in the distal shaft section. A plurality of proximal perfusion ports 21 pass through the walls of the inner and outer tubular members 12 and 15 where they are secured together along said length in the distal section and are in fluid communication with the guidewire receiving perfusion lumen 13. A plurality of distal perfusion ports 22 are provided in the portion of the inner tubular member 12 which extends out the distal end of the balloon 17.

Figure 3:
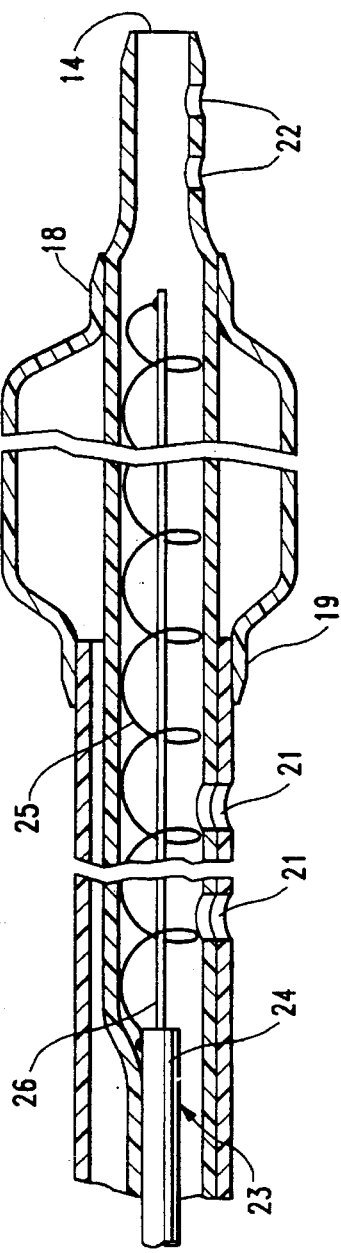
FIG. 3 is a partial longitudinal cross-sectional view of a distal portion of the catheter shown in FIG. 1 with the guidewire receiving perfusion lumen in an expanded condition.
Figure 2:
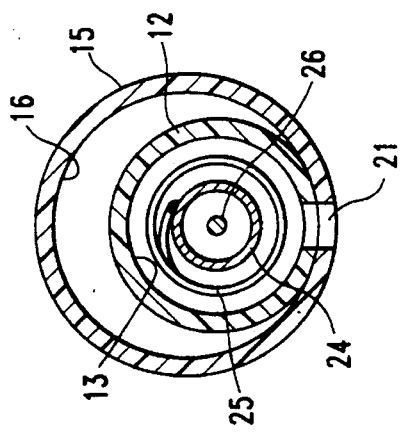
FIG. 2 is a transverse cross-sectional view of the catheter shown in FIG. 1 taken along the lines 2—2.
Figure 4:
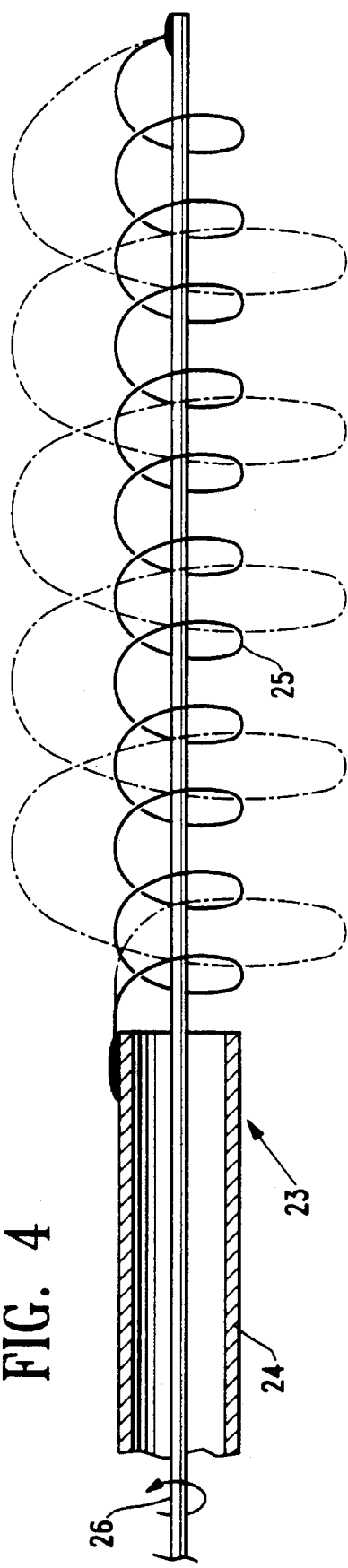
FIG. 4 is an enlarged longitudinal view, partially is section, of the expanding means shown in FIGS. 1–3.

An expanding assembly 23 is disposed within the guidewire receiving perfusion lumen 13 which comprises an elongated high strength tubular member 24, a helical coil 25 secured to the distal end of the high strength tubular member at its proximal end and an elongated operating shaft 26 which extends through the interior of the high strength tubular member and the helical coil and is secured to the distal end of the coil. Relative rotation between the high strength tubular member 24 and the operating shaft 26 causes the expansion and contraction of the coil 25. The expansion of the coil 25 is illustrated in FIG. 3. An enlarged view of the assembly 23 is given in FIG. 5 with the expansion of the coil 25 being shown in phantom. The individual turns of the coil 25 may be stacked adjacent to one another or spaced from each other in the contracted state. Increased spacing between the turns of the coil 25 minimizes the blockage of perfusion parts. If desired, the operating shaft 26 may be moved longitudinally to elastically stretch the coil 25 and to decrease the diametrical dimension of the coil.

The catheter 10 may be advanced over a guidewire into the patient's coronary artery in a conventional manner as previously described in the Background Of The Invention until the balloon 17 is located in a desired position within the patient's coronary artery where the dilatation is to occur. Once in position the guidewire may be removed and the expandable assembly 23 may then be advanced through the perfusion lumen 13 until the expandable coil 25 is disposed within the perfusion lumen. Rotation of the operating shaft 26 expands the coil 25 which in turn expands the perfusion lumen 13 as shown in FIG. 3. The operating shaft 26 may be manually held in the rotated position or a suitable means may be provided to maintain the rotated position with respect to the high strength tubular member 24. The balloon 17 may then be inflated for purposes of dilating the stenotic region of the patient's coronary arteries. When the balloon 17 is inflated during an angioplasty procedure, oxygenated blood is forced to pass through the proximal perfusion ports 21, through the expanded perfusion lumen 13 and then out the distal perfusion ports 22 to provide oxygenated blood distal to the catheter 10 and to thereby avoid the generation of or the exacerbation of ischemic conditions in tissue downstream thereof. The high strength tubular member 24 of the expandable assembly 23 is positioned proximal to the perfusion parts 21 before the coil 25 is expanded so as to avoid impeding with blood flow through the perfusion lumen 13. With the expanded perfusion lumen, long term dilatations may be employed.

The dimensions of the dilatation catheter generally follows the dimensions of commercially available dilatation catheters. The overall length may range from about 120 to about 175 cm, typically about 135 cm, the outer diameter of the catheter shaft about 0.03 to about 0.07 inch (0.76–1.78 mm). The diameter of the guidewire receiving perfusion lumen in the unexpanded state is about 0.01 to about 0.02 inch (0.25–0.51 mm) and in the expanded state is typically about 0.01 to about 0.02 inch (0.25–0.51 mm) larger than the unexpanded state. Greater or lesser expansion may be utilized depending upon the dimensions needed for adequate flow.

The overall length of the expanding assembly 23 is approximately the same as the dilatation catheter and preferably is slightly longer, e.g. about 135 to about 195 cm, typically about 150 cm. The high strength tubular member 23 is about 90 to about 120 cm in length and about 0.015 to about 0.026 inch (0.15–0.46 mm) in outer diameter. The wall thickness ranges from about 0.001 to about 0.003 inch (0.023–0.076 mm) if the tubular member is formed of stainless steel, but other wall thicknesses may be utilized with materials of different tensile strengths. The coil 25 should be long enough to expand at least a significant portion of the perfusion lumen 13 and is preferably long enough to extend from a location proximal to the proximal perfusion ports to a location near the distal end of the balloon e.g. about 10 to about 40 cm in length. The outer diameter of the coil 25 in the unexpanded condition should be about 0.01 to about 0.02 inch (0.25–0.51 mm). The transverse dimensions of the wire forming the coil 25 will vary depending upon the forces needed to expand the portion of the inner tubular member 12 defining the perfusion lumen 13. If formed of conventional 304 stainless steel, the wire is preferably flatwire, typically 0.0025 inch×0.01 inch (0.06×0.25 mm). The operating shaft 26 is longer, e.g. about 10 to about 20 cm longer, than the combined lengths of the high strength tubular member 23 and the coil 25 and may be formed of conventional 304 stainless steel wire about 0.006 to about 0.012 inch (0.15–0.3 mm) in diameter. It also may be formed of a superelastic NiTi alloy. The diametrical dimensions may be varied depending upon the tensile strength of the material. For example, if the operating shaft 26 is formed of a Co—Ni—Cr—Mo type alloy, which has tensile strengths greater than 300 ksi, its diameter may be reduced considerably. Further information concerning the Co—Ni—Cr—Mo type alloys can be found in copending application Ser. No. 08/280,209, filed on Jul. 25, 1994, which is incorporated herein in its entirety by reference. A suitable commercially available alloy is the alloy designated as MP35N (Carpenter Technology Corporation) which has a nominal composition of about 35% cobalt, about 35% nickel, about 20% chromium and about 10% molybdenum.

The method of bonding the inner tubular member 12 to the interior of the outer tubular member 15 and the proximal and distal ends 18 and 19 of the balloon 17 may be effected in a variety of conventional ways. For example, the components may be heat or fusion bonded or bonded by a suitable adhesive such an a epoxy or cyanoacrylate adhesive. To the extent not otherwise described, the catheter and the expandable means of the invention may be formed by conventional techniques used in manufacturing intravascular catheters and guidewires.

Figure 6:
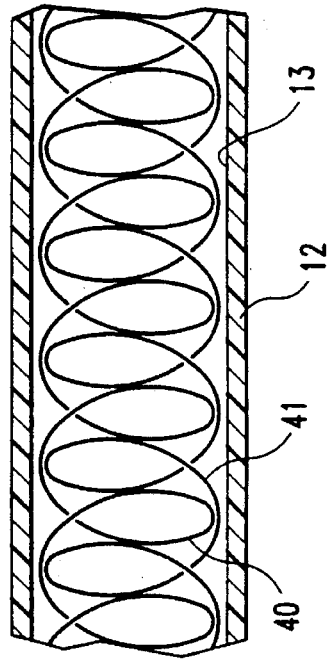
FIG. 6 is a partial longitudinal cross-section of an alternative embodiment of the invention wherein the expanding means is a pair of helical coils having shape memory which are oppositely wrapped.
Figure 5:
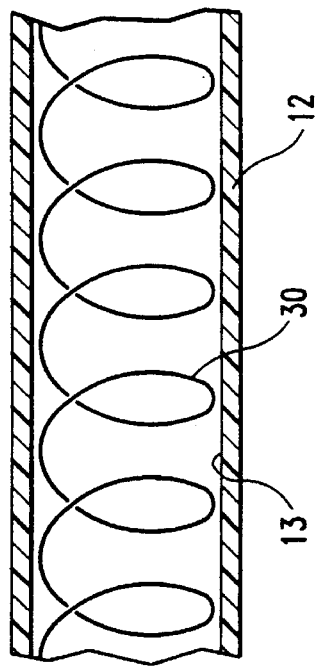
FIG. 5 is a partial longitudinal cross-sectional view of an alternative embodiment of the invention-wherein the expanding means is a coil having shape memory.

FIG. 5 depicts an alternative embodiment of the invention wherein a coil 30 formed of shape memory alloy such as NiTi alloy with 50% (atomic) Ni and 50% (atomic) Ti is disposed within the perfusion lumen 13 of inner tubular which expands at or above body temperature. The alloy formulation and the thermonmechanical processing can be varied to obtain the tensile strength needed which provides adequate expansion of the perfusion lumen at the remembered expanded shape. Moreover, the alloy formulation and thermomechanical processing may also be varied to control the final transformation temperature from the martensite phase to the austenite phase, i.e. the $A_f$ temperature. The remembered shape in the austenite phase is the expanded state and the contracted state is in the martensite phase. Raising the temperature of the shape memory alloy to above the $A_f$ temperature transforms the deformed martensite phase back into the remembered shape in the austenite phase. Details of the alloy formulation and the thermomechanical processing for NiTi alloys are well known to those skilled in the metallurgical arts. For a shape memory alloy with an $A_f$ temperature at body temperature, the alloy must be maintained at a temperature below body temperature by suitable insulation until the catheter is in the desire position within the patient's coronary artery. Once in position and perfusion begins the temperature of the alloy quickly rises to body temperature and the coil then expands within the perfusion lumen expanding the inner diameter thereof. For the shape memory alloy with an $A_f$ temperature above body temperature, the device can be advanced within the patient's vasculature without special treatments but the shape memory alloy must be heated to a temperature above body temperature to effect the expansion. Resistance or inductive heating of the coil may be employed to raise the temperature of the coil. A variety of other means may also be employed such as injecting saline at elevated temperature. FIG. 6 depicts a modification of the embodiment shown in FIG. 5 wherein a pair of such coils 40 and 41 are disposed within the perfusion lumen 13 to expand the lumen. More than two coils may be used if desired or needed.

Figure 7:
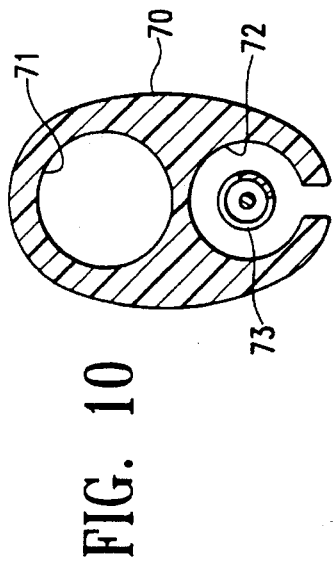
FIG. 7 is a transverse cross-sectional view of an alternative embodiment of the invention wherein the expanding means is a coil or braid incorporated into the wall of the tubular member having shape memory.

Another alternate embodiment is shown in FIG. 7 wherein an expandable braided member 50 formed of a suitable shape memory alloy such as described above is incorporated within the wall of the inner tubular member 12. Expansion of the braided member 50 can be effected in the same fashion as in the prior embodiment.

Figure 8:
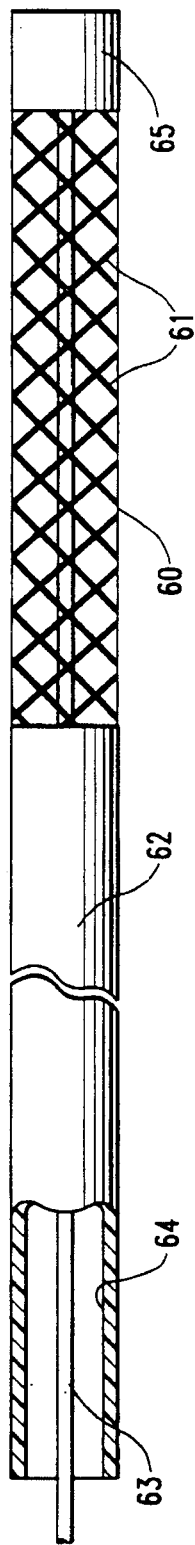
FIG. 8 and 9 are elevational views of an alternative embodiment of the invention wherein the expanding means is a cage which is formed of interwoven high strength strands and which contracts diametrically when the cage is elongated as shown in FIG. 8 and expands diametrically when the cage is shortened as shown in FIG. 9.
Figure 9:
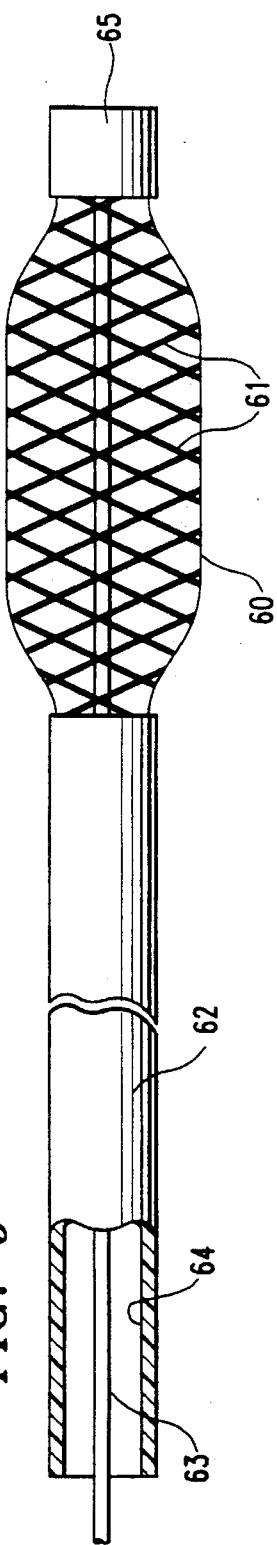

FIGS. 8 and 9 illustrate another alternative embodiment which includes an expandable cage 60 formed of high strength strands 61 such as stainless steel, Co—Ni—Cr—Mo alloys and the like and secured to the distal end of a tubular member 62. A control line 63 extends through the inner lumen 64 of the tubular member 62 and the expandable cage 60 and is secured to a collar 65 secured to the distal end of the cage 60. Applying tension to the control line 63 shortens the length of the cage 60 but in the process of shortening the cage its diameter expands, as shown in FIG. 9. If the strands 61 of the cage 60 are in an unstressed condition when the cage is in the elongated condition and in a stressed condition when the cage is expanded, the control line will only have to apply tension the distal end of the cage 60 to expand the cage and the relaxing of the strands when the tension is remove can be relied upon to return the cage to its elongated condition. In this case the control line 63 may be either flexible or stiff. However, if the expanded cage needs the application of an axial force to return to the elongated condition then the control line must be stiff enough to apply the required axial force.

The tubular member may be formed of suitable high strength materials such as high strength polymeric materials such a polyimide or polyetheretherketone, stainless steel, a pseudoelastic alloy such as NiTi alloy or the Co—Ni—Cr—Mo alloy mentioned above. The control line may be made of the same or similar suitable high strength polymer or metallic materials.

Figure 10:
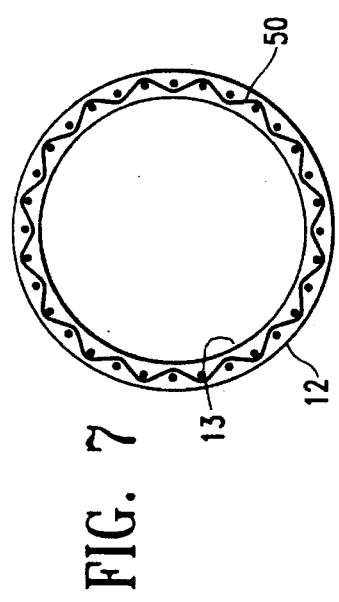
FIG. 10 is a transverse cross-sectional view of an alternative embodiment of the invention wherein the distal section of the catheter shaft containing the perfusion lumen is of a dual lumen design.

FIG. 10 depicts an alternative embodiment of the invention wherein the distal portion of the catheter shaft 70 is of a dual lumen design with an inflation lumen 71 and a guidewire receiving perfusion lumen 72 extending within the distal portion. The expanding device 73 disposed within the perfusion lumen 72 is essentially the same as that shown in FIG. 4.

The present invention has been described herein in terms of dilatation catheters for angioplasty procedures. However, the invention may be utilized in a variety of intravascular catheters. For example, an expandable perfusion lumen 80 may be incorporated into a bail-out catheter 81 as shown in FIG. 11. Perfusion ports 82 are provided in the distal shaft portion 83. The length of the distal portion 83 having perfusion ports is sufficient to extend across a lesion or occlusion with unblocked perfusion ports 82 both proximal and distal to the lesion or occlusion to ensure adequate perfusion into and out of the perfusion lumen 80. Expandable member 85 with. expandable coil 86 is disposed within the perfusion lumen 80 to be expanded in the same manner as the expandable member shown in FIG. 4 to increase perfusion flow through the lumen 80 as in the prior embodiments. As well known by those skilled in the art of interventional cardiology, bail-out devices are employed when an interventional procedure e.g. angioplasty, results in the sudden occlusion of a coronary artery.

Another embodiment of the invention is depicted in FIGS. 12–15. In this embodiment the catheter 90 was a catheter shaft 91 having inner tubular member 92 and outer tubular member 93 disposed about and defining inflation lumen 94 between the inner and outer tubular members. The inner tubular member 92 has a tubular extension 95 formed of an inelastic polymer material such as polyethylene extends from the enlarged distal section 96 and is folded about itself. The perfusion lumen 97 extends through the enlarged distal section 96, through the interior of the balloon 98 to the part 99 in the distal end of the shaft 91. Proximal perfusion parts 100 and distal perfusion parts 101 are provided which are in fluid communication with the perfusion lumen 97.

An expanding assembly 102 is disposed within inner lumen 103 leading to perfusion lumen 97 and the perfusion lumen. The assembly 102 includes a tubular shaft 104 which is preferably formed of hypotubing (conventional stainless steel or a superelastic NiTi alloy) and a coil 105 secured by its proximal end to the distal end of tubular shaft 104. When the catheter 90 is properly disposed within the patient, the expanding assembly 99 is advanced distally to push the coil 105 into the tubular extension 95 thereby expanding the perfusion lumen 97 therein. The proximal portion of the coil 105 is stretched to provide space between the individual turns of the coil so as to avoid blocking the proximal perfusion ports 100 as shown in FIG. 16.

Although individual features of embodiments of the invention may be shown in some of the drawings and not in others, those skilled in the art will recognize that individual features of one embodiment of the invention can be combined with any or all the features of another embodiment. Various modifications and improvements can be made to the present invention without departing the from the scope thereof.

What is claimed is:

1. A perfusion dilatation catheter comprising
   a) an elongated catheter shaft having proximal and distal ends, an inflation lumen extending within a proximal shaft section and a distal shaft section to a discharge location in the distal shaft section spaced proximally from the distal end of the catheter shaft, a perfusion lumen extending at least within the distal shaft section from one or more proximal perfusion openings spaced proximally from the discharge location to an opening in the distal end of the catheter shaft;

b) an inflatable dilatation member on the distal shaft section having an interior in fluid communication with the inflation lumen at the discharge location; and c) expandable tubular means disposed within at least part of the perfusion lumen which has a helical coil having proximal and distal ends, an elongated high strength tubular member having proximal and distal ends and an inner lumen extending therein, with the distal end of the high strength tubular member secured to the proximal end of the helical coil, and an operating shaft having proximal and distal ends, extending within the inner lumen of the high strength tubular member and within the helical coil and having the distal end of the operating shaft secured to the distal end of the coil to increase the transverse cross-sectional area of the perfusion lumen and to thereby increase the flow of blood therethrough.

2. The dilatation catheter of claim 1 wherein the helical coil is expanded by effecting relative axial rotation between the operating shaft and the high strength tubular member to which the coil is secured.

3. The dilatation catheter of claim 1 wherein the expandable tubular means is formed of a shape memory alloy.

4. The dilatation catheter of claim 3 wherein the shape memory alloy has a final transformation temperature of at least body temperature.

5. The dilatation catheter of claim 3 wherein the shape memory alloy has a final transformation temperature above body temperature.

6. A perfusion dilatation catheter comprising a) an elongated catheter shaft having proximal and distal ends, a proximal shaft section, a distal shaft section, an inflation lumen extending within the proximal and distal shaft sections to a discharge location in the distal shaft section spaced proximally from the distal end of the catheter shaft, a perfusion lumen extending at least within the distal shaft section from one or more proximal perfusion openings spaced proximally from the discharge location to an opening in the distal end of the catheter shaft;

b) an inflatable dilatation member on the distal shaft section having an interior in fluid communication with the inflation lumen at the discharge location; and c) an expandable tubular means disposed within the expandable perfusion to increase the transverse cross-sectional area of the perfusion lumen which is an expandable cage having proximal and distal ends and a collar on the distal end and includes an elongated high strength tubular member with proximal and distal ends and an inner lumen extending therein with the proximal end of the cage secured to the distal end of the high strength tubular member, and a control line having proximal and distal ends, extending within the inner lumen of the high strength tubular member and within the cage, with the distal end of the control line being secured to the collar on the distal end of the cage.

7. The dilatation catheter of claim 6 wherein the cage is expanded by applying tension to the proximal end of the control line which extends out of the proximal end of the high strength tubular member to which the cage is secured, the application of tension shortening the length of the cage and expanding the diameter thereof.

8. An intravascular perfusion catheter comprising:

a) an elongated catheter shaft having proximal and distal ends, a port in the distal end of the catheter shaft, an expandable perfusion lumen extending at least within a distal shaft section from one or more proximal perfusion openings in the catheter shaft spaced proximally from the distal end of the catheter shaft to the port in the distal end of the catheter shaft; and b) expandable tubular means disclosed within at least part of the expandable perfusion lumen which has a helical coil having proximal and distal ends, an elongated high strength tubular member having proximal and distal ends and an inner lumen extending therein, with the distal end of the high strength tubular member secured to the proximal end of the helical coil, and an operating shaft having proximal and distal ends, extending within the inner lumen of the high strength tubular member and within the helical coil and having the distal end of the operating shaft secured to the distal end of the coil to increase transverse cross-sectional dimensions of the perfusion lumen along a length thereof between the proximal perfusion opening and the port in the distal end of the catheter shaft to thereby increase the flow of blood therethrough.

9. The intravascular catheter of claim 8 wherein the coil is expanded by effecting relative axial rotation between the operating shaft and high strength tubular member to which the coil is secured.

10. The intravascular catheter of claim 8 wherein the expandable tubular means to increase transverse cross-sectional dimensions of the perfusion lumen is formed of a shape memory alloy.

11. The intravascular catheter of claim 10 wherein the expandable tubular member is incorporated within a wall of a tubular member defining at least part of the perfusion lumen.

12. The intravascular catheter of claim 10 wherein the shape memory alloy has a final transformation temperature at least as high as body temperature.

13. The intravascular catheter of claim 10 wherein the shape memory alloy has a final transformation temperature above body temperature.

14. An intravascular perfusion catheter comprising:

a) an elongated catheter shaft having proximal and distal ends, a port in the distal end of the catheter shaft, an expandable perfusion lumen extending at least within a distal shaft section from one or more proximal perfusion openings in the catheter shaft spaced proximally from the distal end of the catheter shaft to the port in the distal end of the catheter shaft; and b) expandable tubular means to expand the perfusion lumen including an elongated high strength tubular member with proximal and distal ends and an inner lumen extending therein, an expandable cage having proximal and distal ends and a collar on the distal end of the cage, with the proximal end of the cage secured to the distal end of the high strength tubular member, and a control line having proximal and distal ends, extending within the inner lumen of the high strength tubular member and within the cage, with the distal end of the control line being secured to the collar on the distal end of the cage.

15. The intravascular catheter of claim 14 wherein the cage is expanded by applying tension to the proximal end of the control line which extends out of the proximal end of the high strength tubular member to which the cage is secured, the application of tension shortening the length of the cage and expanding the diameter thereof.

16. A perfusion dilatation catheter, comprising:
a) an elongated catheter shaft having proximal and distal ends, an inflation lumen extending within a proximal shaft section and a distal shaft section to a discharge location in the distal shaft section spaced proximally from the distal end of the catheter shaft, a perfusion lumen extending at least within the distal shaft section from one or more proximal perfusion openings spaced proximally from the discharge location to an opening in the distal end of the catheter shaft and being defined by a tubular extension which is capable of being folded about itself to form exterior transverse dimensions which are much smaller than the exterior dimensions of the tubular extension in an expanded condition;
b) an inflatable dilatation member on the distal shaft section having an interior in fluid communication with the inflation lumen at the discharge location; and
c) means to unfold the tubular extension and increase the transverse dimensions of the perfusion lumen defined by the tubular extension to increase blood flow through the perfusion lumen.

17. The dilatation catheter of claim 16 wherein the means to unfold the tubular extension and to increase the transverse dimensions of the perfusion lumen includes a tubular member with proximal and distal ends, an inner lumen extending therein and an inner diameter much larger than the inner diameter of the perfusion lumen extending within the folded tubular extension.

18. The dilatation catheter of claim 17 wherein the tubular member is in the form of a helical coil.

19. The dilatation catheter of claim 18 wherein the helical coil has a stretched proximal section providing space between turns of the coil.

20. A method of performing an angioplasty procedure comprising:
a) providing a dilatation catheter having
an elongated catheter shaft having proximal and distal ends, an inflation lumen extending within a proximal shaft section and a distal shaft section to a discharge location in the distal shaft section spaced proximally from the distal end of the catheter shaft, a perfusion lumen extending at least within the distal shaft section from one or more proximal perfusion openings spaced proximally from the discharge location to an opening in the distal end of the catheter shaft;
an inflatable dilatation member on the distal shaft section having an interior in fluid communication with the inflation lumen at the discharge location; and
an expanding means to increase the transverse cross-sectional area of the perfusion lumen at least within the portion extending within the interior of the inflatable dilatation member;
b) advancing the catheter through a patient's coronary artery until the dilatation balloon on the distal portion is at a desired location within a stenotic region;
c) inflating the dilatation balloon to dilate the stenotic region; and
d) maintaining in an expanded condition at least the portion of the perfusion lumen extending within the interior of the balloon to increase blood flow through the perfusion lumen when the dilatation balloon is inflated.

* * * * *